United States Patent
McDonald et al.

(10) Patent No.: US 9,629,693 B2
(45) Date of Patent: Apr. 25, 2017

(54) DENTAL WEDGE WITH ASYMMETRIC SIDES

(71) Applicant: RHONDIUM IP LIMITED, Katikati (NZ)

(72) Inventors: Simon P. McDonald, Katikati (NZ); Alejandro Aubone, Katikati (NZ); Matthew Backler, Katikati (NZ)

(73) Assignee: Rhondium IP Limited, Katikati (NZ)

( * ) Notice: Subject to any disclaimer, the term of this patent is extended or adjusted under 35 U.S.C. 154(b) by 0 days.

(21) Appl. No.: 14/404,008

(22) PCT Filed: May 31, 2013

(86) PCT No.: PCT/US2013/043733
§ 371 (c)(1),
(2) Date: Nov. 25, 2014

(87) PCT Pub. No.: WO2014/018162
PCT Pub. Date: Jan. 30, 2014

(65) Prior Publication Data
US 2015/0125817 A1    May 7, 2015

(30) Foreign Application Priority Data

May 31, 2012  (NZ) ........................................ 600373
May 3, 2013  (NZ) ........................................ 610160

(51) Int. Cl.
*A61C 7/00*   (2006.01)
*A61C 5/12*   (2006.01)
*A61C 5/88*   (2017.01)

(52) U.S. Cl.
CPC ................ *A61C 5/127* (2013.01); *A61C 5/88* (2017.02)

(58) Field of Classification Search
CPC ........... A61C 5/127; A61C 5/125; A61C 5/85; A61C 5/88
(Continued)

(56) References Cited

U.S. PATENT DOCUMENTS 4,337,041 A * 6/1982 Harsany ................. A61C 5/127
433/149
4,468,199 A * 8/1984 Weikel .................... A61C 5/127
433/149
(Continued)

FOREIGN PATENT DOCUMENTS

DE  19936461 A1  2/2001
DE  10119733 A1  10/2002
(Continued)

*Primary Examiner* — Matthew Nelson
(74) *Attorney, Agent, or Firm* — IpHorgan Ltd.

(57) ABSTRACT

A dental wedge (10) includes symmetrical sides (22, 24). The dental wedge (10) includes a restorative tooth side (24), the restorative tooth side (24) having a generally longitudinally extending planar wall (44) defined in part by an upper edge (34) and a lower edge (42), the planar wall (44) is inclined, wherein the planar wall (44) extends from the lower edge (42) upward and inward. The planar wall (44) includes an upper inclined surface (46) and a lower inclined surface (48), the planar wall (44) having a concave curve extending in a longitudinal direction, the upper inclined surface (46) generally defining the restorative tooth side (24). The wedge (10) further includes an adjacent tooth side (22), the adjacent tooth (22) side having a generally longitudinally extending planar leg (50), the planar leg (50) extends from the lower inclined surface (48) of the planar wall (44) at a location between the upper edge (34) and the lower edge (42), the planar wall (44) and planar leg (50) defining an inverted v-shaped channel (36) extending longitudinally, the planar leg (50) includes a lower edge (40) having a recessed area (30).

18 Claims, 3 Drawing Sheets

(58) Field of Classification Search
USPC .......................................... 433/39, 148–149
See application file for complete search history.

(56) References Cited

U.S. PATENT DOCUMENTS

| | | | |
|---|---|---|---|
| 5,743,738 A | 4/1998 | Baffelli et al. | |
| 5,890,901 A | 4/1999 | Fischer et al. | |
| 6,402,514 B1 | 6/2002 | Fischer et al. | |
| 6,468,080 B1 * | 10/2002 | Fischer | A61C 5/127 433/149 |
| 6,482,007 B2 | 11/2002 | Stanwich et al. | |
| 6,761,562 B2 | 7/2004 | Von Weissenfluh | |
| 7,223,101 B2 | 5/2007 | Garrison et al. | |
| 8,206,151 B2 * | 6/2012 | McDonald | A61C 5/127 433/148 |
| 2002/0055084 A1 * | 5/2002 | Fischer | A61C 5/125 433/149 |
| 2002/0081552 A1 | 6/2002 | Stanwich et al. | |
| 2005/0221255 A1 * | 10/2005 | Haraden | A61C 5/125 433/39 |
| 2005/0272005 A1 | 12/2005 | Schaffner et al. | |
| 2007/0254263 A1 * | 11/2007 | McDonald | A61C 5/127 433/149 |
| 2008/0241787 A1 | 10/2008 | Hegedus | |
| 2011/0171596 A1 | 7/2011 | Clark | |
| 2011/0306007 A1 * | 12/2011 | Ericson | A61C 5/127 433/39 |
| 2012/0058447 A1 * | 3/2012 | Liener | A61C 5/127 433/149 |

FOREIGN PATENT DOCUMENTS

| | | |
|---|---|---|
| DE | 102010040414 A1 | 1/2011 |
| WO | 9909907 | 3/1999 |

\* cited by examiner

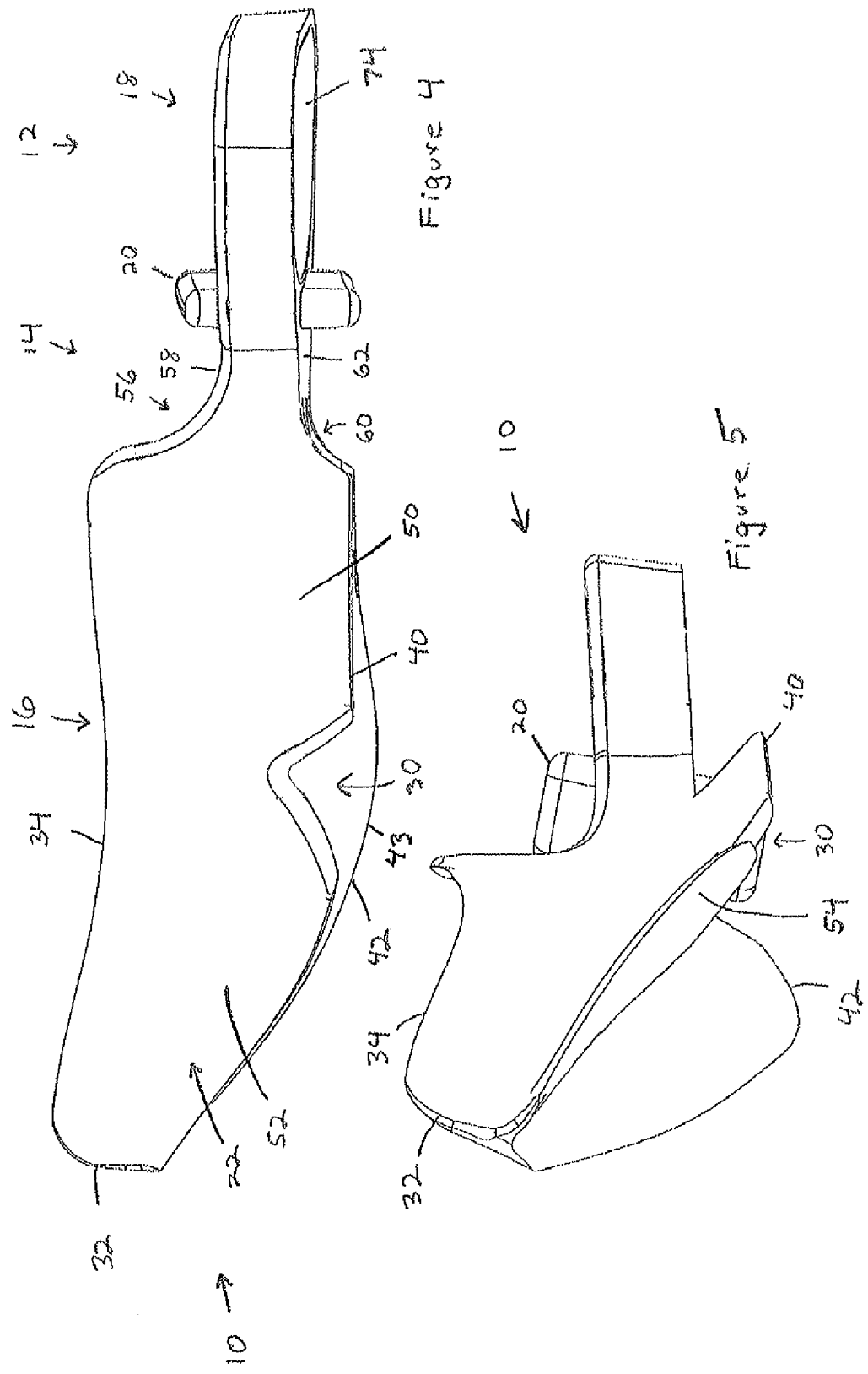

US 9,629,693 B2

DENTAL WEDGE WITH ASYMMETRIC SIDES

CROSS-REFERENCE TO RELATED APPLICATIONS

This application claims the priority to New Zealand Application No. 610160, filed May 3, 2013, and New Zealand Application No. 600373, filed May 31, 2012, the entire contents of which both are hereby incorporated by reference.

FIELD OF THE INVENTION

The present invention relates to a dental wedge, and in particular, a dental wedge used during tooth restoration.

BACKGROUND OF THE INVENTION

A dental wedge is an apparatus used during tooth restoration, usually along with a combination of dental matrix bands and dental matrix band retainers. The main purpose of the dental wedge is to press the dental matrix band against the tooth that is being restored. This allows for the matrix band to seal the tooth and keep the dental restorative material in place. The other purpose of the dental wedge is to separate the teeth and allow enough space for the dentist to restore the tooth. The dental wedge also serves as a gingival margin seal to apply pressure and control bleeding.

Dental wedges are inserted into the interproximal area from the buccal or lingual direction. Initially, dental wedges were made out of wood, but most current dental wedges are plastic. They come in various sizes to suit different interproximal area. Most of the dental wedges have a standard triangular shape.

The standard shape of the dental wedge is not suitable for different tooth restorations. Some tooth restorations require the dental wedge to be of a different shape to better carry out its functions. There is also need of a dental wedge for use during crown placement and other indirect tooth restorations, U.S. Pat. No. 8,206,151 is assigned to the same assignee as the instant application and is an example of assignee's earlier dental wedge.

SUMMARY OF THE INVENTION

It is an object of the present invention to provide a dental wedge that overcomes the problems of the prior art dental wedges.

It is a further object of this invention to provide a device for use during the restoration of a tooth, more specifically the restoration of a crown.

It is another object of this invention to provide a means to block undercuts below the shoulder of a tooth preparation mesially and distally.

It is yet another object of this invention to decrease the time taken to clean a restoration site.

The device is a dental wedge comprising a head portion, a neck portion and a body portion, wherein the neck and body portions have a restorative tooth side and an adjacent tooth side.

The present invention therefore provides a dental wedge having asymmetrical sides. The dental wedge includes a restorative tooth side, the restorative tooth side having a generally longitudinally extending planar wall defined in part by an upper edge and a lower edge, the planar wall is inclined, wherein the planar wall extends from the lower edge upward and inward, the planar wall includes an upper inclined surface and a lower inclined surface, the planar wall having a concave curve extending in a longitudinal direction, the upper inclined surface generally defining the restorative tooth side. The wedge further includes an adjacent tooth side, the adjacent tooth side having a generally longitudinally extending planar leg, the planar leg extends from the lower inclined surface of the planar wall at a location between the upper edge and the lower edge, the planar wall and planar leg defining an inverted v-shaped channel extending longitudinally, the planar leg includes a lower edge having a recessed area.

BRIEF DESCRIPTION OF THE DRAWINGS

FIG. 4 is a left side view of the dental wedge of FIG. 1;

FIG. 5 is a front view the dental wedge of FIG. 1;

DETAILED DESCRIPTION OF THE INVENTION

Figure 1:
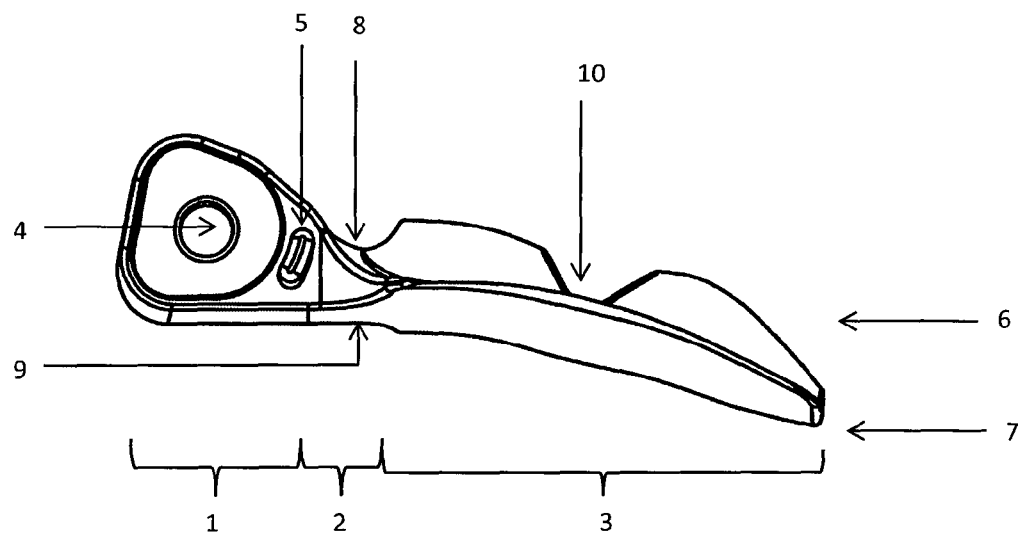
FIG. 1 is a top view of a dental wedge having asymmetrical sides in accordance with one embodiment of the present invention.
Figure 2:
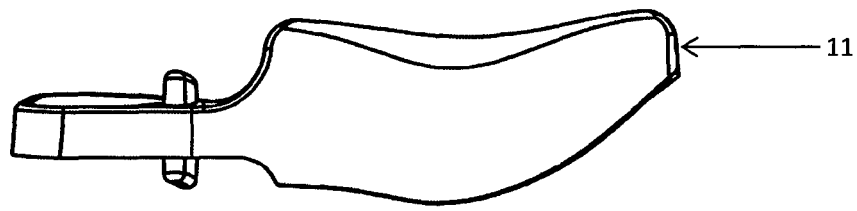
FIG. 2 is a right side view of the dental wedge of FIG. 1.

FIG. 1 shows a dental wedge 10 having asymmetrical sides in accordance with one embodiment of the present invention. The dental wedge of the present invention is available in a variety of sizes. Further, as will be appreciated, the dental wedge of the present invention is provided in right and left orientations. The dental wedges shown in the drawings are all left orientation. The dental wedge 10 consists of a head portion 12, a neck portion 14 and a body portion 16. The head portion 12 has a void or opening 18 that allows for placement of the dental wedge 10 using tweezers that have a pin. The head portion 12 in cross section through the void 18 has an hourglass shape. In particular, the head portion 12 includes a cylindrical wall 70 forming the void 12, a conical shaped upper surface 72 (FIG. 2) extending up from the cylindrical wall 70, and a conical shaped lower surface 74 extending down from the cylindrical wall 70. The configuration around the void 18 allows for the tweezers with a pin to self-locate the void 18. The head portion 12 also has a lug 20 that serves as a grip for normal tweezers during placement.

The neck and body portions 14, 16 have asymmetrical sides as shown by the adjacent tooth side 22 and the restorative tooth side 24. The adjacent tooth side 22 of the neck potion 14 includes a deeply curved portion 26, whereas the restorative tooth side 24 includes a portion 28 which is straight. Optionally, the portion 28 of the restorative tooth side 24 may be marginally curved.

The adjacent tooth side 22 of the body portion 16 has a general wave pattern with a notch 30 at the trough of the wave. The notch 30 increases flexibility of the wedge 10 in the interproximal space and forms a tighter contact with the adjacent tooth. The position of the notch 30 is by the contact point, but on the adjacent tooth side. The notch 30 allows for better adaptation of the wedge 10 around the adjacent tooth.

The restorative tooth side 24 of the body portion 16 has a gentle curve from the neck portion 14 to the tip 32 of the wedge 10. This structure allows for excess dental materials, used during crown placement, to ooze out of the interproximal space. The dental wedge 10 also limits entry of excess dental materials into the interproximal space. This reduces clean up after crown placement, The structure also decreases hindrance from the wedge 10 during crown handling.

The two sides of the body portion 16 join together to form a flat tip 32.

Figure 3:
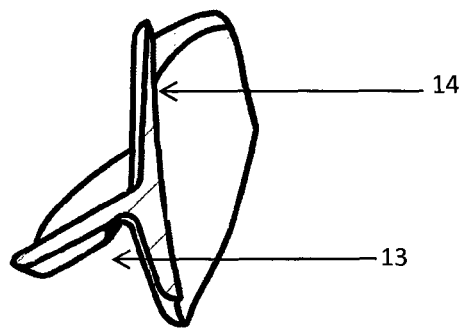
FIG. 3 is a cross-sectional view of the dental wedge of FIG. 1 taken along lines 3-3 of FIG. 2.

In the cross-sectional view, the two sides of the body portion 16 form a disproportionate "T" shape, as shown in the FIG. 3. The disproportionate "T" is made up of a sharp upper edge 34 on the top and a "V" shaped portion 36 at the bottom. The height of the sharp upper edge 34 can vary to accommodate varying heights of the contact points. Optionally, the dentist can modify the height of the sharp upper edge 34 out of the patient's mouth to the required level. The "V" shaped portion 36 has a recessed area 100 which aids in the vertical movement of the dental wedge 10. The "V" shaped portion 36 also provides better adaptation of the wedge against the adjacent tooth.

The disproportionate structure of the two sides 22, 24 of the wedge 10 and the purposeful flex (flexibility created by the notch) included in the wedge 10 allow for the deformation of the wedge 10. These features allow the wedge 10 to better fill the interproximal space and form tighter contact with the adjacent tooth. The disproportionate structure also allows for the tilt of the wedge 10 towards the adjacent tooth. The tilt prevents the formation of undercuts and aids in the formation of better contact points on the restorative tooth.

FIG. 4 shows a left side view of the dental wedge 10. The lower edge 40 of the adjacent tooth side 22 is shown. The lower edge 42 of the restorative tooth side 24 is also shown. The view shows the notch 30 provided at the trough of the wave like shaped lower edge 40. The lower edge 42 of the restorative tooth side 24 includes an apron-like shape that provides an extended portion 43 in comparison to the prior art. The extended portion 43 provides better adaption in dental restorations that have a central deepest point. The lower edge 42 prevents the wedge from invading the central deepest point of the tooth preparation space and prevents the formation of a ledge on the restoration.

FIGS. 3-5 show that the restorative tooth side 24 includes a generally longitudinally extending planar wall 44 having an inclined surface 46 with a generally upper orientation and an inclined surface 48 having a generally lower orientation. The adjacent tooth side 22 includes a generally longitudinally extending planar leg 50 having an upper inclined surface 52 and a lower inclined surface 54. FIG. 4 also shows a curved upper edge 56 which extends from the sharp upper edge 34 and widens and blends into a horizontal top side 58 of the neck portion 14 and head portion 12. FIG. 4 also shows a curved lower edge 60 which extends from the lower edge 40 of the adjacent tooth side 22 and blends into a horizontal bottom side 62 of the neck portion 14 and head portion 12.

The dental wedge 10 works such that the dentist prepares the tooth for restoration in the usual manner. The dentist places the dental wedge 10 on either side of the tooth to be restored. The dentist selects and adjusts the crown to fit mesially and distally. Dental cement is used to cement the crown to the prepared tooth. When the crown is pressed onto the prepared tooth, the excess cement oozes out. The dental wedge 10 directs the flow of cement to the buccal and lingual areas. The buccal and lingual areas are easier to clean up than the interproximal areas around the restoration site as the dentist has better access. The dental wedge 10 is removed with minimal clean up at the restoration site, especially in the interproximal area.

Figure 6:
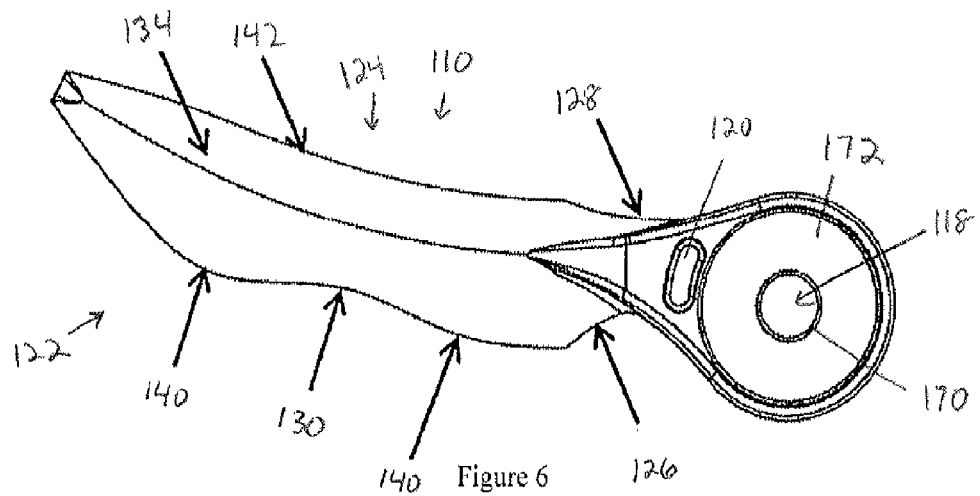
FIG. 6 is a top view of a dental wedge having asymmetrical sides in accordance with another embodiment of the present invention.
Figure 7:
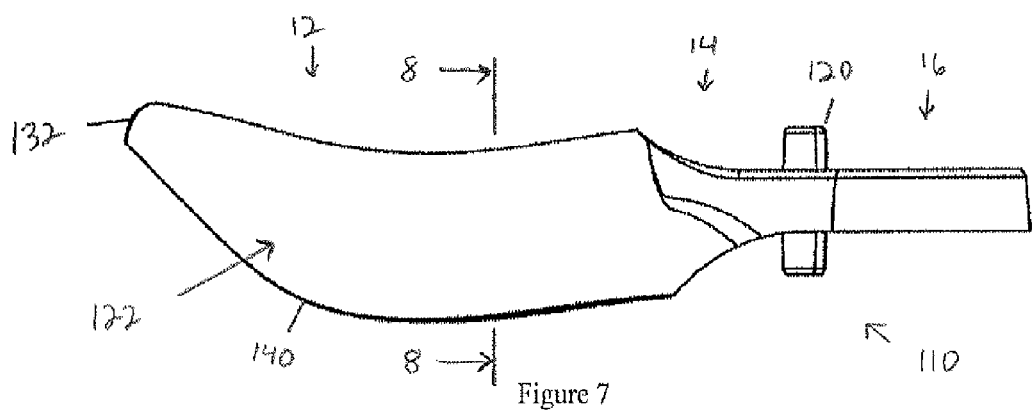
FIG. 7 is a left side view of the dental wedge of FIG. 6.
Figure 8:
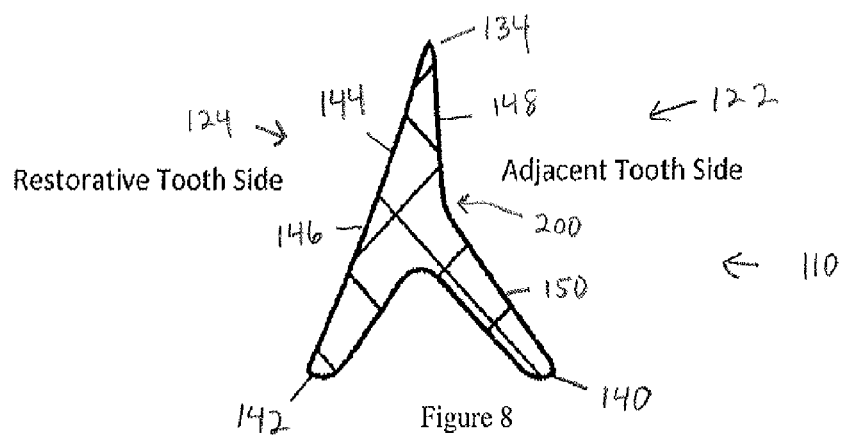
FIG. 8 is a cross-sectional view of the dental wedge of FIG. 6 taken along lines 8-8 of FIG. 7.

FIGS. 6-8 show a dental wedge 110 of the present invention in accordance with another embodiment. The dental wedge 110 of FIGS. 6-8 provides a trough 130 rather than a notch 30. The trough 130 and notch 30 as well as similar structures are generally referred to as a recessed area 30 or 130. As will be appreciated, similar features are identified with similar references and are used interchangeably.

The dental wedge 110 consists of a head portion 112, a neck portion 114, and a body portion 116. The head portion has a void 118 that allows for placement of the dental wedge using tweezers that have a pin. The head portion also has a lug 120 that serves as a grip for normal tweezers during placement.

The neck and the body portions have asymmetrical sides. One side of the wedge is for the adjacent tooth side 122 and the other side is for the restorative tooth side 124. The adjacent tooth side of the neck portion includes a deeply curved portion 126 whereas the restorative tooth side includes a marginally curved portion 128.

The adjacent tooth side of the body portion has two wings or wave shape with a trough 130 therebetween. The adjacent tooth fits in the trough 130 formed by the wings. The main purpose of this side is to spring against the adjacent tooth. The restorative tooth side of the body portion has a gentle curve from tip 132 to neck portion 114. This is to stop the dental materials, used during crown placement, from oozing into the interproximal area and reduce clean up afterwards. This side also allows for crown handling without interferences from the wedge 110. The two sides of the body portion join together to form a 'Y' shape cross section as shown in FIG. 8. The 'Y' is made up of a sharp edge 134 on the top and an inverted 'V' shape at the bottom. The sharp edge 134 aids the restorative tooth side in stopping dental material from oozing out. The sharp edge 134 has a recess 200 which aids in the vertical movement of the wedge. It also provides better adaptation against the adjacent tooth. The 'V' shape aids the adjacent tooth side with its spring action. The "V" shape straddles the papilla and protects it. It also allows the wedge 110 to sit lower within the embrasure to block out undercuts and to prevent excess dental material from oozing into this area.

As seen in FIG. 7, the two lower edges 140, 142 of the body portion curve up and converge at tip 132 to allow for easy insertion of the dental wedge.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

We claim:

1. A dental wedge having asymmetrical sides, the dental wedge comprising:

a restorative tooth side (24), the restorative tooth side having a generally longitudinally extending wall (44), the wall is generally flat in cross section, the wall is defined in part by an upper edge (34) and a lower edge (42), the wall is inclined, wherein the wall extends from the lower edge upward and inward, the wall includes an upper inclined surface (46) and a lower inclined surface (48), the wall having a concave curve extending in a longitudinal direction, the upper inclined surface generally defining the restorative tooth side; and an adjacent tooth side (22), the adjacent tooth side having a generally longitudinally extending leg (50), the leg extends from the lower inclined surface (48) of the wall (44) at a location between the upper edge (34) and the lower edge (42), the extending leg (50) spaced apart from the upper edge (34), the leg is generally flat in cross section, the wall and leg defining an inverted v-shaped channel (36) extending longitudinally, the leg includes a lower edge (40) having a recessed area (30).

2. The dental wedge of claim 1, wherein the dental wedge is made of a generally flexible material.

3. The dental wedge of claim 1, wherein the dental wedge includes a head portion (12), a neck portion (14) and a body portion (16), wherein the restorative tooth side and the adjacent tooth side are formed in the body portion (16).

4. The dental wedge of claim 3, wherein the body portion (16) terminates at a flat tip (32), and the lower edges (40, 42) of the wall (44) and the leg (50) curve up toward the flat tip (32) in a converging manner.

5. The dental wedge of claim 3, wherein the wall and leg include a transition portion at the neck portion, wherein the wall (44) includes a curved upper edge (56) and curved lower edge (64) and the leg includes a curved lower edge (62), wherein the curved lower edges (62, 64) extend upward and toward the head portion (12) in a curved manner before blending into a lower horizontal surface (62) of the neck portion, the curved upper edge (56) extends downward and toward the head portion (12) in a curved manner before blending into an upper horizontal surface (58) of the neck portion, the neck portion and the head portion include a sidewall (66) on the restorative tooth side, the sidewall is formed in part by the curved upper edge (56) and curved lower edge (64) of the wall, wherein the sidewall blends into and is an extension of the wall, and further wherein the curved lower edge of the leg further extends in a curved manner inwardly and towards the head portion.

6. The dental wedge of claim 3 wherein the lower edges (40, 42) extend across the body portion (16) in a curved manner and having a crest at approximately a mid-portion of the body portion.

7. The dental wedge of claim 3 wherein the cross-section of the body portion (16) resembles an inclined T-shape, with the leg (50) forming the stem of the T-shape.

8. The dental wedge of claim 3 wherein the cross-section of the body portion (16) resembles an inverted Y-shape, with an upper portion of the wall (44) forming the stem of the Y-shape.

9. The dental wedge of claim 3, wherein the head portion includes an opening (18) to receive a tweezer with a pin, and a gripping lug (20) for manipulation by a tweezer.

10. The dental wedge of claim 1, wherein the dental wedge includes a head portion, a neck portion and a body portion, wherein the restorative tooth side and the adjacent tooth side are formed in the body portion (16) and the neck portion (14).

11. The dental wedge of claim 1, wherein the recessed area of the leg is a notch (30).

12. The dental wedge of claim 1, wherein the dental wedge provides a resilient spring-like resistance to compressive forces.

13. The dental wedge of claim 1, wherein the dental wedge is a one-piece molded component.

14. The dental wedge of claim 1, wherein the dental wedge is made of plastic.

15. The dental wedge of claim 1, wherein the inverted v-shaped channel (36) includes a recessed area (100), wherein the recessed area aids in the vertical movement of the wedge and provides a better adaptation of the wedge against the adjacent tooth.

16. The dental wedge of claim 1, wherein the upper edge (34) includes a recess (200), wherein the recessed area aids in the vertical movement of the wedge and provides a better adaptation of the wedge against the adjacent tooth.

17. The dental wedge of claim 1, wherein the lower edge (42) includes an extended portion (43), wherein the extended portion (43) is capable of preventing a dental wedge from invading a central deepest point of a tooth preparation space and preventing the formation of a ledge on a restoration.

18. The dental wedge of claim 9, wherein the opening (18) in the head portion is formed by a cylindrical wall (70), a conical shaped upper surface (72) extending up from the cylindrical wall (70), and a conical shaped lower surface (74) extending down from the cylindrical wall (70).

* * * * *